(12) United States Patent
Feucht et al.

(10) Patent No.: US 7,651,978 B2
(45) Date of Patent: *Jan. 26, 2010

(54) SELECTIVE HERBICIDES BASED ON A SUBSTITUTED PHENYLSULPHONYLAMINOCARBONYL-TRIAZOLINONE

(75) Inventors: Dieter Feucht, Monheim (DE); Hans-Joachim Santel, Leawood, KS (US); Klaus Lürssen, Bergisch-Gladbach (DE); Ingo Wetcholowsky, Estancia Marambaia (BR); Peter Dahmen, Neuss (DE); Klaus-Helmut Müller, Düsseldorf (DE)

(73) Assignee: Arysta LifeScience North America, LLC, Cary, NC (US)

( * ) Notice: Subject to any disclaimer, the term of this patent is extended or adjusted under 35 U.S.C. 154(b) by 155 days.

This patent is subject to a terminal disclaimer.

(21) Appl. No.: 10/393,359

(22) Filed: Mar. 21, 2003

(65) Prior Publication Data

US 2004/0063585 A1 Apr. 1, 2004

Related U.S. Application Data

(62) Division of application No. 09/806,338, filed as application No. PCT/EP99/06989 on Sep. 21, 1999, now Pat. No. 6,562,760.

(30) Foreign Application Priority Data

Oct. 2, 1998 (DE) ................................. 198 45 407

(51) Int. Cl.
*A01N 47/28* (2006.01)
*A01N 47/38* (2006.01)
*C07D 405/00* (2006.01)

(52) U.S. Cl. ....................... 504/273; 504/193; 548/110; 548/263.4

(58) Field of Classification Search .................. 504/273, 504/193; 548/110, 263.4
See application file for complete search history.

(56) References Cited

U.S. PATENT DOCUMENTS 5,057,144 A 10/1991 Daum et al. .................... 71/92
5,534,486 A * 7/1996 Muller et al. ................ 504/273
5,652,372 A * 7/1997 Muller et al. ............. 548/263.4

FOREIGN PATENT DOCUMENTS

| CA | 2027206 | 12/1997 |
|---|---|---|
| CA | 2064636 | 12/1997 |
| EP | 0 341 489 | 8/1995 |
| EP | 0 931 456 | 7/1999 |
| WO | 98/12923 | 4/1998 |

OTHER PUBLICATIONS

Database Cropu, V.M. Sorensen, et al.: "Control of Wild Oat (Aveda Fatua), Green Foxtail (*Setarial viridis*) and Selected Broadleaf Weeds in Spring Wheat With Flucarbazone-Sodium" retrieved from STN-International accession No. 199-85011 Cropu, XP002126658, Zusammenfassung & Abstr. Meed Sci. Soc. Am., Nr. 39, 1999, Seite 8.

Database Cropu, H.J., Santel et al.: "Flucarbazone-Sodium: a New Herbicide for Grass Control In Wheat" retrieved from STN-International, accession No. 1999-85010 Cropu, XP002126659, Zusammenfassung & Bstr. Meet. Weed Sci. Soc. Am., Bd. 39, 1999, Seite 7.

* cited by examiner

*Primary Examiner*—Mina Haghighatian
(74) *Attorney, Agent, or Firm*—Pillsbury Winthrop Shaw Pittman LLP

(57) ABSTRACT

The present invention relates to selective-herbicidal compositions, characterized in that they contain an effective amount of the compound 2-(2-trifluoromethoxy-phenylsulphonylaminocarbonyl)-4-methyl-5-methoxy-2,4-dihydro-3H-1,2,4-triazol-3-one of the formula (I)

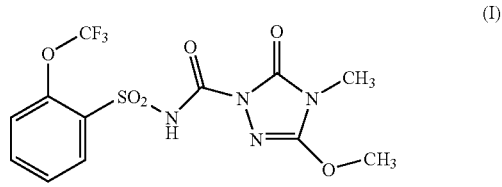

(I)

and/or of salts of the compound of the formula (I), and to the use of these compositions for the selective control of weeds in crops of cereals, in particular crops of wheat, and to methods for the selective control of weeds in crops of cereals by applying the compositions together with surfactants and/or customary extenders.

6 Claims, No Drawings

SELECTIVE HERBICIDES BASED ON A SUBSTITUTED PHENYLSULPHONYLAMINOCARBONYL-TRIAZOLINONE

This is a divisional of application Ser. No. 09/806,338 filed May 14, 2001, which is a 371 of International Application No. PCT/EP99/06989 filed Sep. 21, 1999 now U.S. Pat. No. 6,562,760; the disclosures of which are incorporated herein by reference.

The invention relates to the use of the known compound 2-(2-trifluoromethoxy-phenylsulphonylaminocarbonyl)-4-methyl-5-methoxy-2,4-dihydro-3H-1,2,4-triazol-3-one of the formula (I) shown below—alias 4,5-dihydro-3-methoxy-4-methyl-5-oxo-N-[[2-(trifluoromethoxy)-phenyl]-sulphonyl]-1H-1,2,4-triazol-1-carboxamide (CAS-Reg.-No.: 145026-88-6)—and its salts, in particular its sodium salt (CAS-Reg.-No. 181274-17-9), for the selective control of weeds in crops of useful plants, in particular for controlling problematic weeds in cereals.

Substituted phenylsulphonylaminocarbonyltriazolinones such as, for example, the compounds 2-(2-trifluoromethoxy-phenylsulphonylaminocarbonyl)-4-ethyl-5-methoxy-2,4-dihydro-3H-1,2,4-triazol-3-one, 2-(2-trifluoromethoxy-phenylsulphonylaminocarbonyl)-4-methyl-5-ethoxy-2,4-dihydro-3H-1,2,4-triazol-3-one, 2-(2-trifluoromethoxy-phenylsulphonylaminocarbonyl)-4-methoxy-5-methyl-2,4-dihydro-3H-1,2,4-triazol-3-one, 2(2-trifluoromethyl-phenylsulphonylaminocarbonyl)-4-methyl-5-methoxy-2,4-dihydro-3H-1,2,4-triazol-3-one and 2-(2-difluoromethoxy-phenylsulphonylaminocarbonyl)-4-methyl-4-methoxy-2,4-dihydro-3H-1,2,4-triazol-3-one and their salts, processes for preparing these compounds and their use as herbicides are the subject of earlier patent applications (cf. EP-341 489, EP-422 469, EP-507 171, U.S. Pat. No. 5,534,486). The individual abovementioned substituted phenylsulphonylaminocarbonyltriazolinones have a molecular structure which is very similar to that of the compound (I) to be used according to the invention but, in contrast to this compound, they show shortcomings in their activity or activity gaps in the case of certain weeds.

Surprisingly, it has now been found that the compound 2-(2-trifluoromethoxy-phenylsulphonylaminocarbonyl)-4-methyl-5-methoxy-2,4-dihydro-3H-1,2,4-triazol-3-one (I) and salts thereof, in particular the sodium salt of the compound of the formula (I), in comparison with the abovementioned structurally similar compounds, show considerably stronger activity against some weeds in cereal crops which are difficult to control, combined with very good compatibility with cereal species, such as, in particular, wheat, and are therefore particularly suitable for the efficient and selective control of weeds in cereals, in particular in wheat. The activity gaps observed with the abovementioned comparative compounds which are closely related to (I) do not occur in the weed spectrum of the compound (I) and its salts.

The invention provides selective-herbicidal compositions, characterized in that they contain an effective amount of the compound 2-(2-trifluoromethoxy-phenylsulphonylaminocarbonyl)-4-methyl-5-methoxy-2,4-dihydro-3H-1,2,4-triazol-3-one of the formula (I)

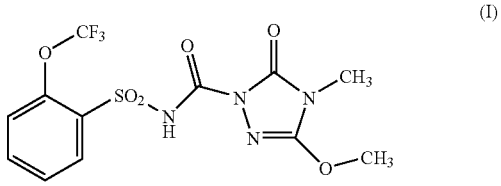

and/or of salts of the compound of the formula (I), in particular of their sodium salt [referred to as "(I)-Na-salt" in the use examples].

The invention furthermore provides the use of the compound 2-(2-trifluoromethoxy-phenylsulphonylaminocarbonyl)-4-methyl-5-methoxy-2,4-dihydro-3H-1,2,4-triazol-3-one of the formula (I)—above—and/or of salts of the compound of the formula (I), in particular of its sodium salt, for the selective control of weeds in crops of cereals, in particular in crops of wheat.

The invention furthermore provides a method for the selective control of weeds in crops of cereals, in particular in crops of wheat, which is characterized in that the compound 2-(2-trifluoromethoxy-phenylsulphonylaminocarbonyl)-4-methyl-5-methoxy-2,4-dihydro-3H-1,2,4-triazol-3-one of the formula (I)—above—and/or salts of the compound of the formula (I), in particular its sodium salt, is/are applied with surfactants and/or customary extenders in crops of cereals.

The compound of the formula (I) and its Na salt are already known (cf. U.S. Pat. No. 5,534,486—Examples 79 and 321).

The compound of the formula (I) and its salts have a broad herbicidal activity. They can be used, for example, for controlling the following weeds:

Dicotyledonous weeds of the orders: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Monocotyledonous weeds of the orders: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera, Aegilops, Phalaris.

However, the use of the compound (I) and its salts is by no means limited to these orders but extends in the same manner to other plants as well.

The compound of the formula (I) and its salts have strong herbicidal activity and a broad spectrum of activity when used on the soil and on above-ground parts of plants. They are suitable for the selective control of monocotyledonous and dicotyledonous weeds in monocotyledonous crops, especially in cereals, in particular in wheat, both by the pre-emergence and by the post-emergence method.

Problematic weeds which can be controlled particularly well with the compound of the formula (I) and its salts, in particular its sodium salt, and whose control is less likely to succeed with both conventional herbicides and more recent compounds of a similar molecular structure are, in particular, *Agropyron, Alopecurus, Amaranthus, Apera, Avena, Brassica, Bromus, Capsella, Digitaria, Echinochloa, Erysimum,*

*Lolium, Matricaria, Phalaris, Poa, Polygonum, Setaria, Sinapis, Thlaspi* and *Veronica*.

The compound of the formula (I) and its salts, in particular its sodium salt, can be converted into the customary formulations, such as solutions, emulsions, wettable powders, suspensions, powders, dusts, pastes, soluble powders, granules, suspension/emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water, it is also possible to employ for example organic solvents as auxiliary solvents. Suitable liquid solvents are essentially the following: aromatics, such as xylene, toluene or alkylnaphthalenes, chlorinated aromatics, such as chlorobenzenes, chlorinated aliphatics, such as chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colourants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For the control of weeds, the compound of the formula (I) and its salts, as such or in the form of their formulations, can also be used as mixtures with known herbicides, finished formulations or tank mixes being possible.

Possible components for the mixtures are known herbicides, for example amidosulfuron, bentazon, bromoxynil, carfentrazone(-ethyl), cinidon(-ethyl), clodinafop(-propargyl), clopyralid, chlorsulfuron, chlortoluron, cyclosulfamuron, 2,4-D, diclofop(-methyl), difenzoquat, diflufenican, florasulam, flupyrsulfuron(-methyl, -sodium), pyraflufen(-ethyl), ethoxyfen, fenoxaprop(-ethyl), fluoroglycofen(-ethyl), flupropacil, fluroxypyr, iodosulfuron, isoproturon, mecoprop, metosulam, metribuzin, metsulfuron(-methyl), pendimethalin, prosulfocarb, pyridate, sulfosulfuron, thifensulfuron(-methyl), tralkoxydim, triasulfuron, tribenuron(-methyl), trifluralin.

Mixtures with other known active compounds, such as fungicides, insecticides, acaricides, nematicides, bird repellents, plant nutrients and agents which improve soil structure, are also possible.

The compound of the formula (I) and its salts can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The compound of the formula (I) and its salts can be applied either before or after emergence of the plants. They can also be incorporated into the soil before sowing.

The amount of active compound used can vary within a substantial range. It depends essentially on the nature of the desired effect. In general, the amounts used are between 1 g and 1 kg of active compound per hectare of soil surface, preferably between 5 g and 0.5 kg per ha.

The use of the compound of the formula (I) and its salts can be seen from the following examples.

Use Examples:

In the use examples, the compounds shown below are used as comparative substances:

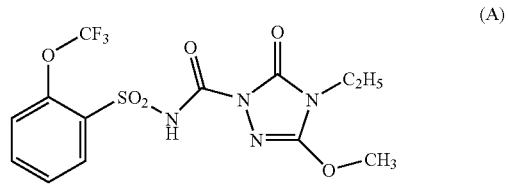

(A)

2-(2-Trifluoromethoxy-phenylsulphonylaminocarbonyl)-4-ethyl-5-methoxy-2,4-dihydro-3H-1,2,4-triazol-3-one (known from EP-507 171, U.S. Pat. No. 5,534,486—Example 87)

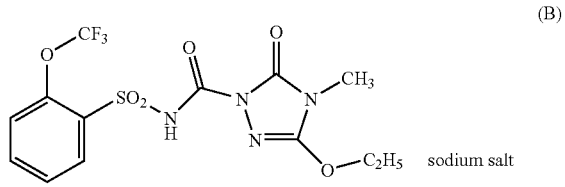

(B)

2-(2-Trifluoromethoxy-phenylsulphonylaminocarbonyl)-4-methyl-5-ethoxy-2,4-dihydro-3H-1,2,4-triazol-3-one—sodium salt—(known from U.S. Pat. No. 5,534,486—Example 260)

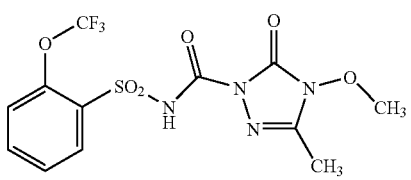
(C)

2-(2-Trifluoromethoxy-phenylsulphonylaminocarbonyl)-4-methoxy-5-methyl-2,4-dihydro-3H-1,2,4-triazol-3-one (known from EP-422 469—Example 96; see also U.S. Pat. No. 5,057,144—Example 96)

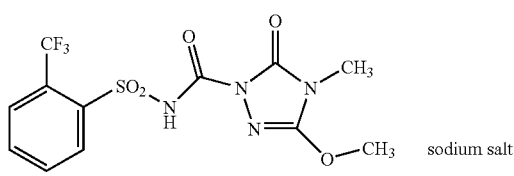
(D)

2-(2-Trifluoromethyl-phenylsulphonylaminocarbonyl)-4-methyl-5-methoxy-2,4-dihydro-3H-1,2,4-triazol-3-one—sodium salt (known from EP-507 171, U.S. Pat. No. 5,534,486—Example 187)

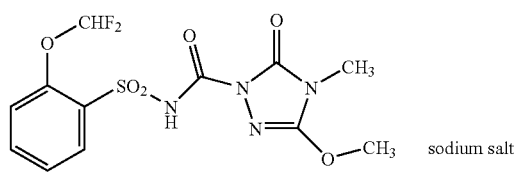
(E)

2-(2-Difluoromethoxy-phenyl sulphonylaminocarbonyl)-4-methyl-5-methoxy-2,4-dihydro-3H-1,2,4-triazol-3-one—sodium salt (known from U.S. Pat. No. 5,534,486—Example 319)

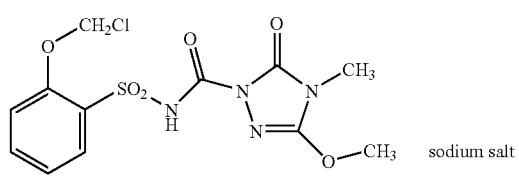
(F)

2-(2-Chlorodifluoromethoxy-phenylsulphonylaminocarbonyl)-4-methyl-5-methoxy-2,4-dihydro-3H-1,2,4-triazol-3-one—sodium salt (in the claim of EP-507 171 and U.S. Pat. No. 5,534,486)

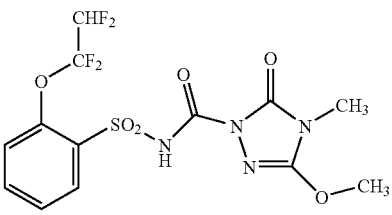
(G)

2-[2-(1,1,2,2-Tetrafluoroethoxy)-phenylsulphonylaminocarbonyl]-4-methyl-5-methoxy-2,4-dihydro-3H-1,2,4-triazol-3-one (in the claim of EP-507 171 and U.S. Pat. No. 5,534,486)

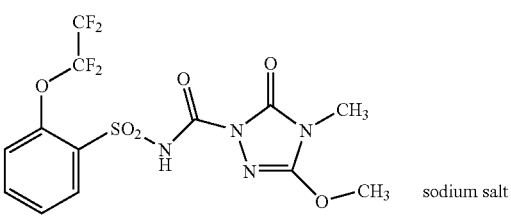
(H)

2-[2-(Pentafluoroethoxy)-phenylsulphonylaminocarbonyl]-4-methyl-5-methoxy-2,4-dihydro-3H-1,2,4-triazol-3-one—sodium salt (in the claim of EP-507 171 and U.S. Pat. No. 5,534,486)

EXAMPLE A

Pre-Emergence Test/Greenhouse

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 500 ml of water per hectare.

After three weeks, the degree of damage to the plants is assessed in % damage in comparison to the development of the untreated control.

The figures denote:

0%=no effect (like untreated control)

100%=total destruction

In this test, for example, the sodium salt of the compound of the formula (I) exhibits, at an application rate of from 30 g/ha, very strong activity (efficacy 80% to 100%) against weeds, such as, for example, Alopecurus, Avena, Bromus, Digitaria, Echinochloa, Matricaria, Polygonum and Setaria, combined with very good compatibility with crop plants, such as, for example, wheat, whereas the comparative compounds (A), (C), (D), (E) and (F) exhibit considerably weaker herbicidal activity and the comparative compound (B) is not compatible with wheat (cf. Table A1). The considerable superiority of (I)-Na-salt over the comparative compound (G) is shown in Table A2 ["ai."="active ingredient"].

amount of solvent, the stated amount of emulsifier is added and the concentrate is diluted with water to the desired concentration.

Test plants which have a height of 5-15 cm are sprayed with the preparation of active compound such that the particular amounts of active compound desired are applied per unit area.

TABLE A1

| | | Pre-emergence test/greenhouse | | | | | | | | |
|---|---|---|---|---|---|---|---|---|---|---|
| Active compounds | Application rate (g of ai./ha) | Wheat | Alopecurus | Avena | Bromus | Digitaria | Echinochloa | Setaria | Matricaria | Polygonum |
| (A) | 30 | 0 | 20 | 0 | 40 | 0 | 50 | 60 | 0 | 0 |
| (B) | 30 | 50 | 70 | 80 | — | — | — | — | — | 80 |
| (C) | 30 | 0 | 0 | 0 | 0 | 0 | 0 | 0 | 0 | 0 |
| (D) | 30 | 0 | 70 | 50 | — | 80 | — | — | 30 | 70 |
| (E) | 30 | 0 | 50 | 30 | 0 | 40 | 30 | 80 | 0 | 60 |
| (F) | 30 | 0 | 90 | 40 | 95 | 80 | 80 | 95 | 50 | 0 |
| (I)-Na-salt | 30 | 0 | 100 | 95 | 100 | 100 | 80 | 100 | 100 | 90 |

TABLE A2

| | Pre-emergence test/greenhouse | | | |
|---|---|---|---|---|
| Active compounds | Application rate (g ai./ha) | Alopecurus | Avena | Setaria |
| (G) | 250 | 50 | 0 | 50 |
| (I)-Na-salt | 250 | 100 | 99 | 99 |

EXAMPLE B

Post-Emergence Test/Greenhouse

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated The concentration of the spray liquor is chosen so that the particular amounts of active compound desired are applied in 500 ml of water/ha.

After three weeks, the degree of damage to the plants is assessed in % damage in comparison to the development of the untreated control.

The figures denote:

0%=no effect (like untreated control)

100%=total destruction

In this test, for example, the sodium salt of the compound of the formula (I) exhibits, at an application rate of 60 g/ha, strong activity (efficacy 70% to 100%) against weeds, such as, for example, Agropyron, Alopecurus, Avena, Bromus, Lolium, Setaria and Veronica, combined with very good compatibility with crop plants, such as, for example, wheat, whereas the comparative compounds (A), (B), (C), (D), (E) and (F) have considerably weaker herbicidal activity (cf. Table B1). A considerable superiority of (I)-Na-salt (at 125 g/ha) over the comparative compounds (G) and (H) (in each case at 250 g/ha!) is shown in Table B2.

TABLE B1

| | | Post-emergence test/greenhouse | | | | | | | |
|---|---|---|---|---|---|---|---|---|---|
| Active compounds | Application rate (g ai./ha) | Wheat | Agropyron | Alopecurus | Avena | Bromus | Lolium | Setaria | Veronica |
| (A) | 60 | 0 | 0 | 0 | 0 | 40 | 0 | 40 | — |
| (B) | 60 | 0 | — | 40 | — | — | 70 | — | 70 |
| (C) | 60 | 0 | 0 | 0 | 0 | 0 | 0 | 0 | 0 |
| (D) | 60 | 0 | — | — | — | — | — | — | 0 |
| (E) | 60 | 0 | 60 | 20 | 70 | 0 | 20 | — | 30 |
| (F) | 60 | 10 | — | 70 | 70 | 90 | 70 | 70 | 80 |
| (I)-Na-salt | 60 | 0 | 70 | 80 | 70 | 90 | 90 | 100 | 90 |

TABLE B2

Post-emergence test/greenhouse

| Active compounds | Application rate (g ai./ha) | Alopecurus | Avena | Setaria |
|---|---|---|---|---|
| (G) | 250 | 30 | 0 | 30 |
| (H) | 250 | 40 | 80 | 20 |
| (I)-Na-salt | 125 | 90 | 90 | 95 |

EXAMPLE C

Post-Emergence Tests/Outdoors

In addition to the comparative compounds (B) and (D), the sodium salt of the compound of the formula (I) was tested under outdoor conditions in the main cultivation areas of summer wheat in Canada against economically important weeds. The small-plot experiments were carried out on cultivated land under agricultural use. Areas with particularly extensive weed growth were chosen preferably.

The active compounds were applied across the area by the spray method, with an average droplet size. To produce a useful preparation of active compound, the active compounds were formulated as 70 WP (70% w/w water-dispersible powder) and applied with customary amounts of water. Wetting of the plants was improved by addition of a surface-active substance (SAS) in the concentrations recommended by the respective manufacturer.

To assess the crop compatibility, from 1 to 8 weeks after the treatment, plant growth inhibitions or ailing of the leaf area were assessed in % damage in comparison to the development of the untreated control. At different intervals after the treatment, the herbicidal activity was assessed as % reduction in comparison to the untreated control, based on the weed development. The figures denote:

0%=no damage of the crops or no herbicidal effect,

100%=total destruction of the crops or the weeds.

The tests that were carried out show that the sodium salt of the compound of the formula (I) has considerably stronger activity against Avena fatua than the comparative compounds (B) and (D), combined with approximately the same compatibility.

["% w/w"=percentage by weight]

TABLE C

Post-emergence tests/outdoors

| Test plants | Number of tests | herbicidal effect (%) (B) + SAS (30 g of a.i./ha) | herbicidal effect (%) (D) + SAS (15 g of a.i./ha) | herbicidal effect (%) (I)-Na-salt + SAS (30 g of a.i./ha) |
|---|---|---|---|---|
| Avena fatua | 6 | 69 | 65 | 88 |
| Setaria viridis | 5 | 95 | 81 | 94 |
| Fallopia convolvulus | 5 | 71 | 70 | 73 |
| Sinapis arvensis | 5 | 97 | 95 | 94 |
| Thlaspi arvense | 3 | 97 | 95 | 93 |
| Crop damage (wheat) | 9 | 5 | 12 | 6 |

SAS = "Canplus 411" (commercial product)

EXAMPLE D

Post-Emergence Tests/Outdoors

The sodium salt of the compound of the formula (I) was tested under outdoor conditions in the main cultivation areas of summer wheat in Canada and the USA against economically important weeds. The small-plot experiments were carried out on cultivated land under agricultural use, with cultivation and climate conditions which can be considered to be representative for the period of the trial. Areas with particularly extensive weed growth were chosen by way of preference.

The active compound was applied across the area by the spray method, with an average droplet size. To produce a useful preparation of active compound, the active compound was formulated as 70 WP or 70 WG (70% w/w water-dispersible powder or granules) and applied with customary amounts of water. Wetting of the plants was improved by addition of a surface-active substance (SAS) in the concentration recommended by the manufacturer.

To assess the crop compatibility, from 1 to 8 weeks after the treatment, plant growth inhibitions or ailing of the leaf area were assessed in % damage in comparison to the development of the untreated control. At different intervals after the treatment, the herbicidal activity was assessed as % reduction in comparison to the untreated control, based on the weed development. The figures denote:

0%=no damage of the crops or no herbicidal effect,

100%=total destruction of the crops or the weeds.

The tests that were carried out show that the sodium salt of the compound of the formula (I) is particularly suitable for controlling Avena fatua, Setaria viridis, Amaranthus retroflexus, Brassica spp., Capsella bursa-pastoris, Sinapis arvensis and Thlaspi arvense in cereals.

TABLE D

Post-emergence tests/outdoors

| Test plants | Number of tests | (I)-Na-salt + SAS (28–30 g of a.i./ha) herbicidal effect (%) |
|---|---|---|
| Avena fatua | 263 | 90 |
| Setaria viridis | 102 | 94 |
| Amaranthus retroflexus | 60 | 90 |
| Brassica spp. | 27 | 93 |
| Capsella bursa-pastoris | 12 | 90 |
| Sinapis arvensis | 48 | 98 |
| Thlaspi arvense | 45 | 97 |
| Crop damage (wheat) | 408 | 3 |

SAS = Agral, Agsurf, Canplus 411, X-77 (commercial products)

The invention claimed is:

1. A method for the selective control of weeds comprising adding a selective herbicidal composition comprising an effective amount of a sodium salt of the compound 2-(2-trifluoromethoxy-phenylsulphonyl-aminocarbonyl)-4-methyl-5-methoxy-2,4-dihydro-3H-1,2,4-triazol-3-one of the formula (I),

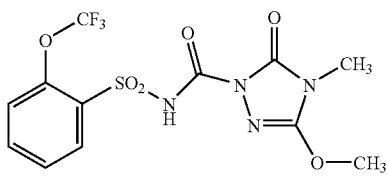

to a cereal crop and/or its environment.

2. A method for the selective control of weeds comprising adding a selective herbicidal composition comprising an effective amount of a sodium salt of the compound 2-(2-trifluoromethoxy-phenylsulphonyl-aminocarbonyl)-4-methyl-5-methoxy-2,4-dihydro-3H-1,2,4-triazol-3-one of the formula (I),

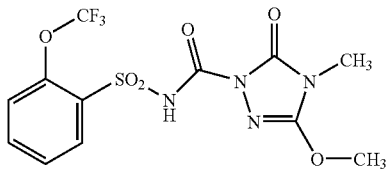

to a wheat crop and/or its environment.

3. The method of claim 1, wherein the composition comprises 70% w/w water dispersable powder or granules of the sodium salt of the compound 2-(2-trifluoromethoxy-phenyl-sulphonyl-aminocarbonyl)-4-methyl-5-methoxy-2,4-dihydro-3H-1,2,4-triazol-3-one of the formula (I),

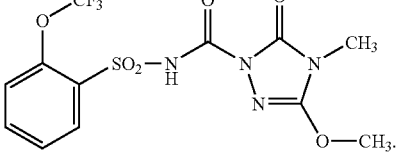

4. The method of claim 1, wherein the composition further comprises a surfactant or an extender.

5. The method of claim 2, wherein the composition comprises 70% w/w water dispersable powder or granules of the sodium salt of the compound 2-(2-trifluoromethoxy-phenyl-sulphonyl-aminocarbonyl)-4-methyl-5-methoxy-2,4-dihydro-3H-1,2,4-triazol-3-one of the formula (I),

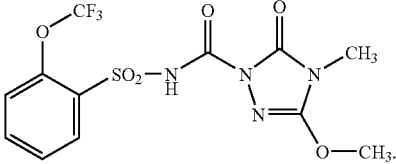

6. The method of claim 2, wherein the composition further comprises a surfactant or an extender.

* * * * *